(12) United States Patent
Bao

(10) Patent No.: US 12,601,724 B2
(45) Date of Patent: Apr. 14, 2026

(54) WATER ALKALINITY DETECTION SYSTEM

(71) Applicant: Tien-I Bao, Taoyuan City (TW)

(72) Inventor: Tien-I Bao, Taoyuan City (TW)

( * ) Notice: Subject to any disclaimer, the term of this patent is extended or adjusted under 35 U.S.C. 154(b) by 235 days.

(21) Appl. No.: 18/382,541

(22) Filed: Oct. 23, 2023

(65) Prior Publication Data

US 2024/0060951 A1    Feb. 22, 2024

Related U.S. Application Data

(63) Continuation-in-part of application No. 16/951,751, filed on Nov. 18, 2020, now abandoned.

(51) Int. Cl.
| | |
|---|---|
| *G01N 3/18* | (2006.01) |
| *G01N 1/14* | (2006.01) |
| *G01N 31/16* | (2006.01) |
| *G01N 33/18* | (2006.01) |

(52) U.S. Cl.
CPC .............. *G01N 33/18* (2013.01); *G01N 1/14* (2013.01); *G01N 31/16* (2013.01)

(58) Field of Classification Search
None
See application file for complete search history.

(56) References Cited

FOREIGN PATENT DOCUMENTS

CN          114518427 A   *   5/2022   ........... G01N 31/164

* cited by examiner

*Primary Examiner* — J. Christopher Ball

(57)          ABSTRACT
A water alkalinity detection system includes an installing box having a reference sink, a test sink and a temporary sink. A pH value detecting probe is positioned in the test sink and serves to test a liquid inputted into the test sink for detecting a pH value of the liquid. A reference pumping device serves to pump a reference liquid of the reference sink into the test sink. A temporary pumping device serves to pump an external liquid of an external sink into the temporary sink. A transferring pumping device serves to pump the external liquid from the temporary sink into the test sink. An air pumping device is connected to the test sink and the temporary sink. A control device includes a processor serving to calculate an external KH value of the external liquid.

15 Claims, 10 Drawing Sheets

WATER ALKALINITY DETECTION SYSTEM

The invention is a continuation in part (CIP) of the U.S. patent application Ser. No. 16/951,751 filed at Nov. 18, 2020, which is assigned to the inventor of the present invention, and thus the contents of the U.S. patent application Ser. No. 16/951,751 is incorporated into the present invention as a part of the specification.

FIELD OF THE INVENTION

The present invention is related to a water testing system, and in particular to a water alkalinity detection system.

BACKGROUND OF THE INVENTION

Alkalinity (KH) is very an important factor for keeping corals and marine fish in the water of a tank. Keepers must regularly test the KH value of the water and raise it appropriately if needed. In the prior arts, the KH value of the water of the tank can be measured by colorimetry titration or acid-base indicator titration. However, both colorimetry titration and acid-base indicator titration use an acid solution added to the water to be measured, which will cause higher costs due to regularly buying the acid solution, and will cause irreversible chemical changes of the measured water. Therefore, the measured water cannot be poured back into the tank for reuse. The water of the tank is cultivated through a complicated process. Frequently taking out the water from the tank for measuring the KH value will quickly consume the water of the tank, which causes a problem that the keeper must regularly repeat the complicated process for cultivating new water for the tank.

There is another method for measuring the KH value, which is performed by that an air is injected to the samples of a solution to be measured and a reference solution having a known KH value until both solution approach to a stable state, and then analyze the pH values of both solution to obtain the KH value of the solution to be measured. Both solutions can be poured into the tank for reuse because no irreversible chemical change is produced during measuring. However, this method must be tested and compared manually, which is very inconvenient and easy to cause failing of the process of cultivating water in the tank.

SUMMARY OF THE INVENTION

Accordingly, the object of the present invention is to provide a water alkalinity detection system, wherein the present invention has a control device capable of obtaining the KH value of the external liquid in an external sink at any time and adjusting the KH value of the external liquid in the external sink automatically by using a liquid titration device and titration parameters stored in an electronic device. The KH value of the external liquid is obtained by just pumping air into the reference liquid and the external liquid and detecting the pH values of the reference liquid and the external liquid, no titration portion or reagent is needed, which saves the cost of titration portion and reagent and avoids polluting the external sink by any chemicals of the titration portion and reagent. Therefore, the present invention can be used for auto detecting and adjusting the KH value of an external sink having a seawater used for culturing organisms. Moreover, the reference liquid and the external liquid tested will be pumped back to the reference sink and the external sink respectively, which do not cause any wasting of reference liquid or external liquid.

To achieve above object, the present invention provides a water alkalinity detection system comprising: an installing box having a reference sink, a test sink and a temporary sink; the reference sink having a reference liquid which has a predetermined KH (alkalinity) value; a pH value detecting probe positioned in the test sink and serving to test a liquid inputted into the test sink for detecting a pH value of the liquid in the test sink; three liquid pumping devices which are a reference pumping device, a transferring pumping device and a temporary pumping device, respectively; the reference pumping device being connected to the reference sink and the test sink; the transferring pumping device being connected to the test sink and the temporary sink; the temporary pumping device being connected to the temporary sink and serving to be connected to an external sink which has an external liquid to be tested; the reference pumping device serving to pump the reference liquid of the reference sink into the test sink; the temporary pumping device serving to pump the external liquid of the external sink into the temporary sink; the transferring pumping device serving to pump the external liquid inputted to the temporary sink into the test sink; an air pumping device connected to the test sink and the temporary sink; the air pumping device serving to pump air into the test sink and the temporary sink simultaneously; a control device connected to the liquid pumping devices and the pH value detecting probe; wherein in detecting, the control device serves to control the air pumping device to pump the air into the reference liquid inputted to the test sink and the external liquid inputted to the temporary sink simultaneously for a predetermined period of time to form a processed reference liquid in the test sink and a processed external liquid in the temporary sink; the pH value detecting probe is controlled by the control device to detect a reference pH value of the processed reference liquid; the control device serves to control the reference pumping device to pump the processed reference liquid tested by the pH value detecting probe from the test sink back into the reference sink to empty the test sink, and to control the transferring pumping device to pump the processed external liquid from the temporary sink into the test sink emptied by the reference pumping device; the pH value detecting probe is controlled by the control device to detect an external pH value of the processed external liquid inputted into the test sink; and the control device including a processor; the processor serving to receive the reference pH value and the external pH value detected by the pH value detecting probe and to calculate an external KH value of the processed external liquid according to the KH value of the reference liquid, the reference pH value and the external pH value.

3

Figure 7:
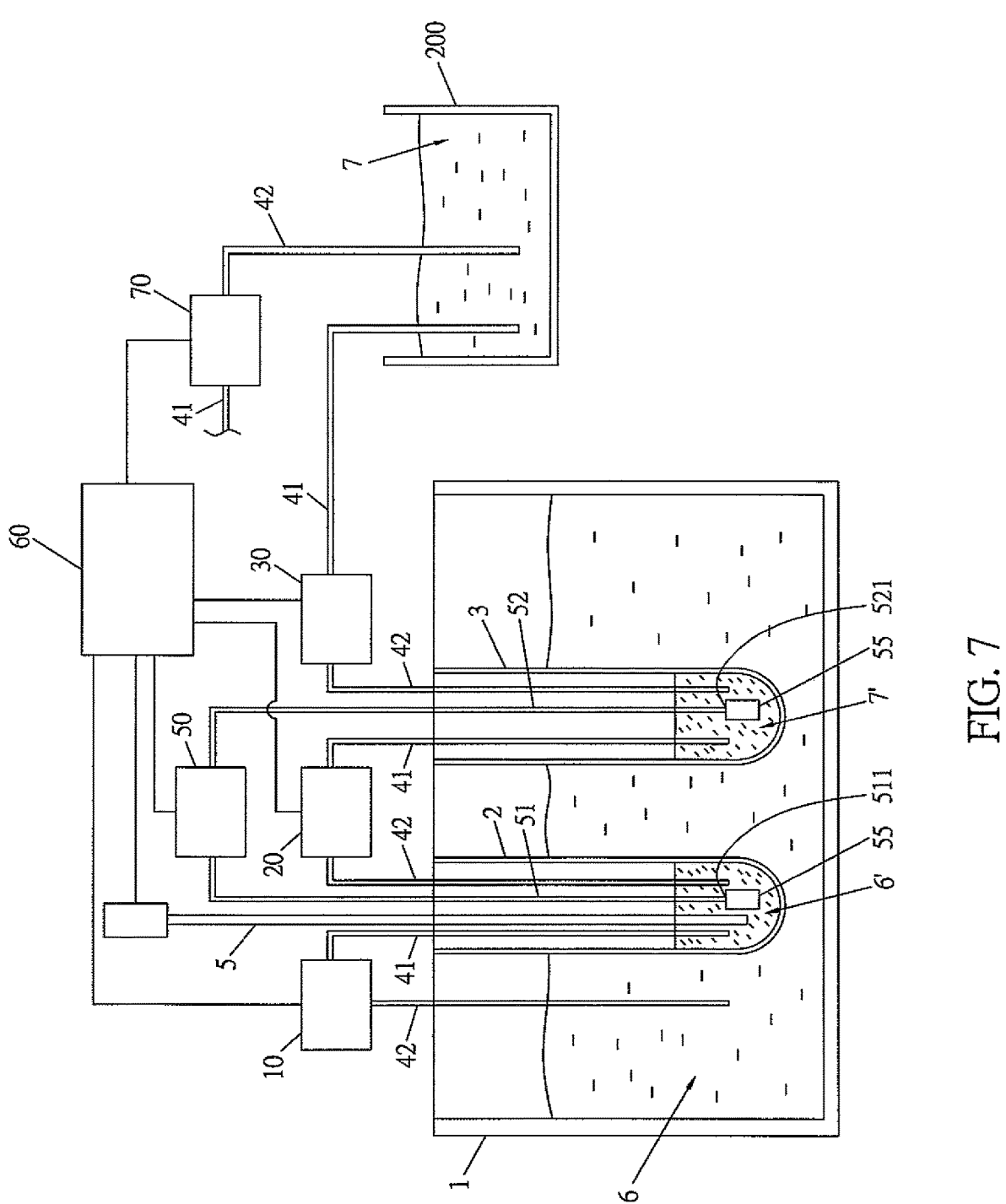

FIG. 7 is a schematic view showing another operating state of the present invention, wherein the processed reference liquid and the processed external liquid are formed in the test sink and the temporary sink respectively.

Figure 8:
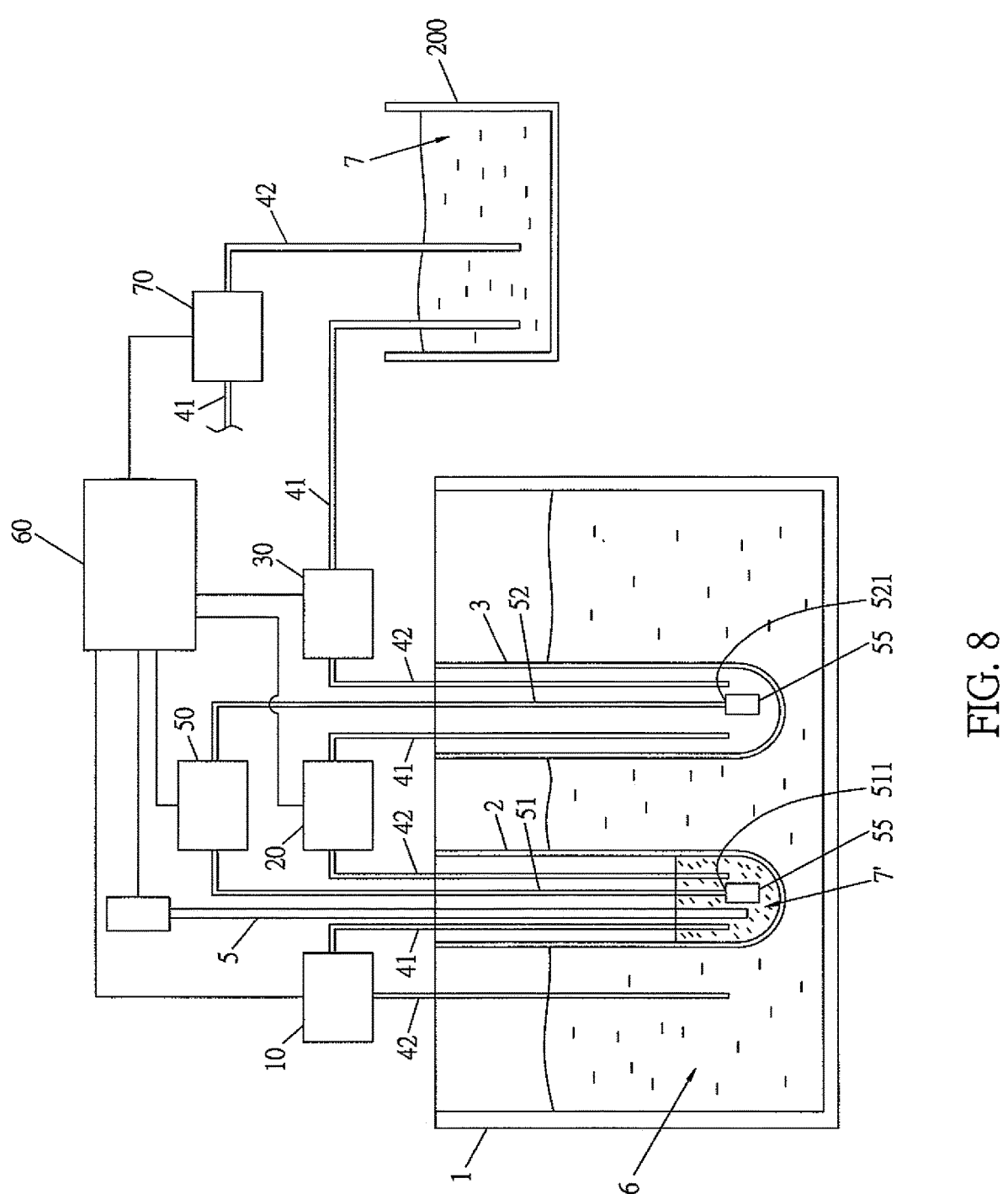

FIG. 8 is a schematic view showing another operating state of the present invention, wherein the processed external liquid is pumped into the test sink for detecting the external pH value.

Figure 9:
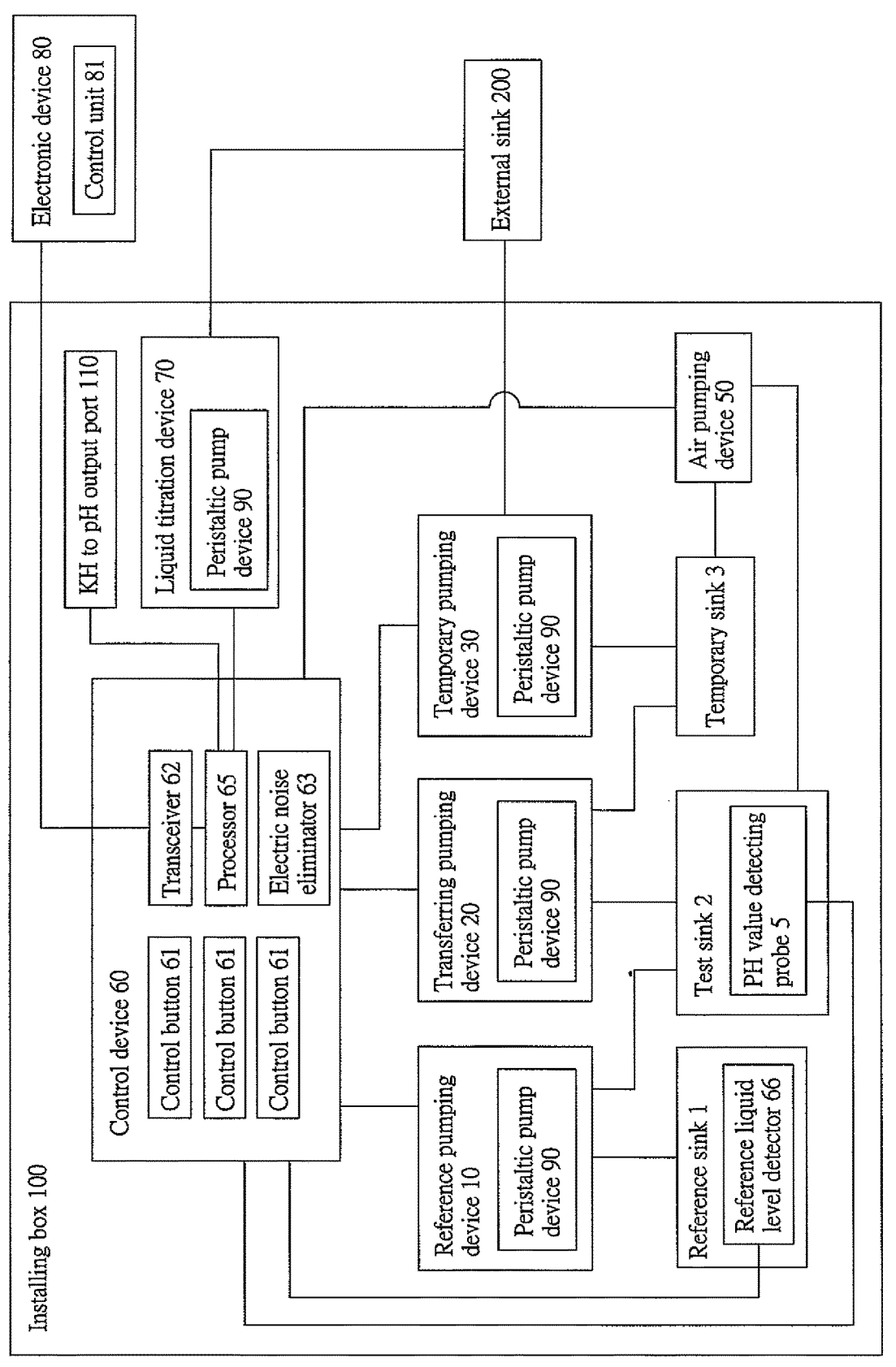

FIG. 9 is a structural block diagram of the elements of the present invention.

Figure 10:
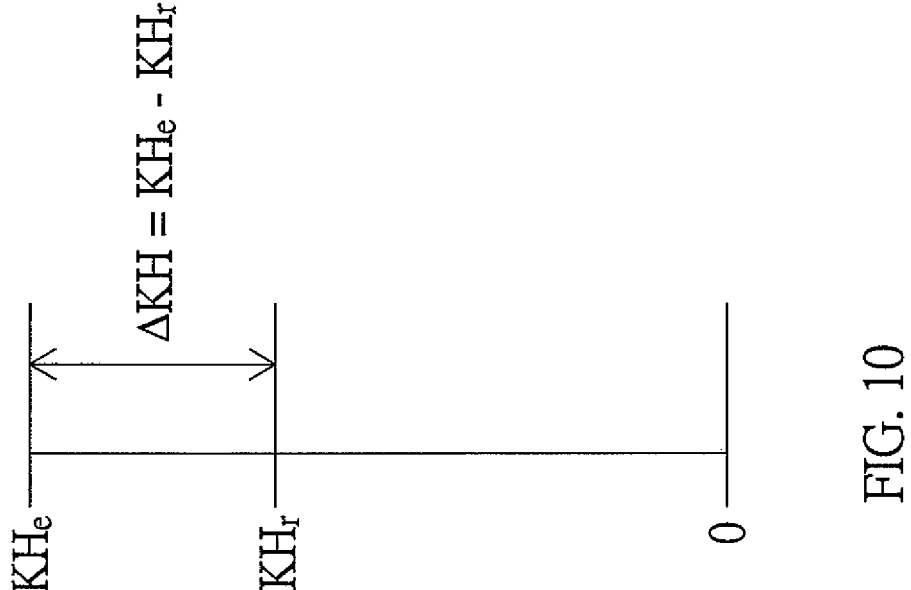

FIG. 10 is a schematic view showing the relation between the external KH value and the KH value of the reference liquid.

DETAILED DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

With reference to FIGS. 1 to 10, the structure of the present invention is illustrated. The present invention includes the following elements.

Figure 1:
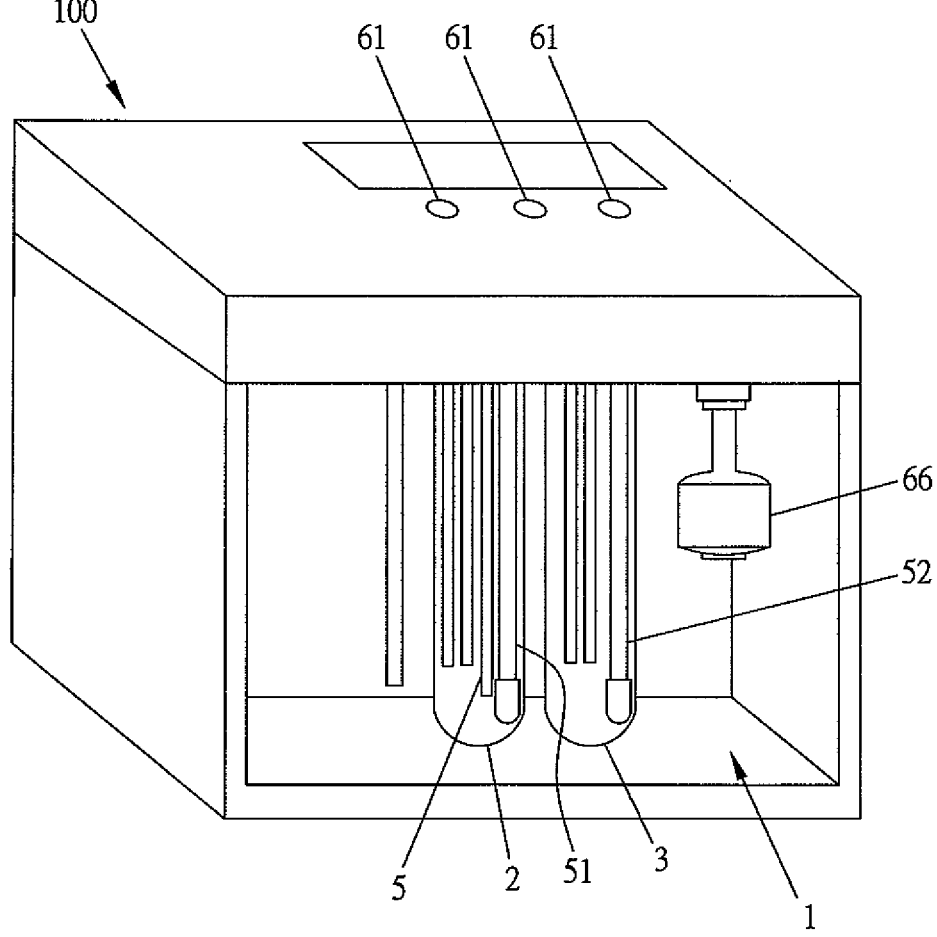
FIG. 1 is an assembly schematic view of the elements of the present invention.
Figure 6:
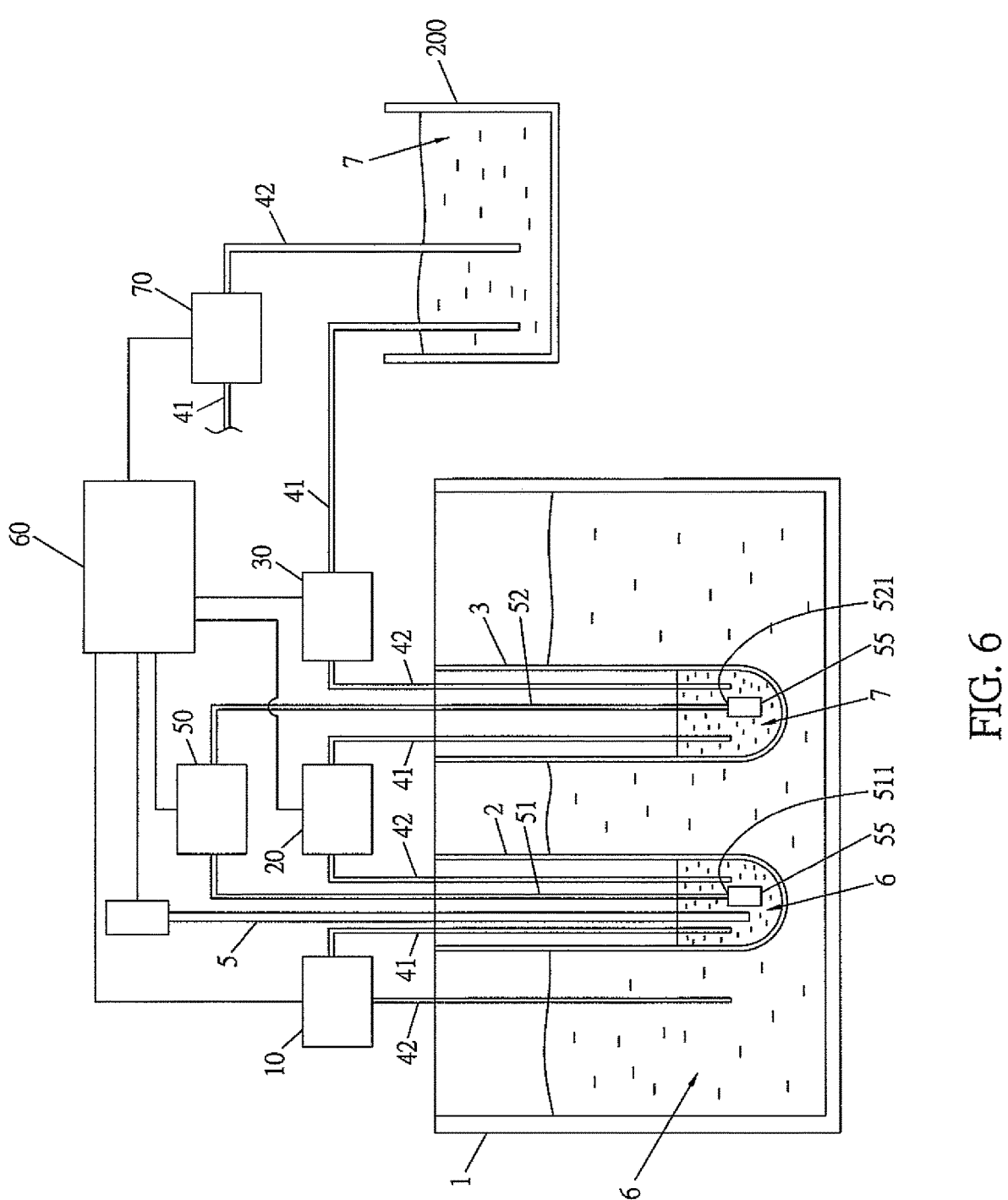
FIG. 6 is a schematic view showing an operating state of the present invention, wherein the reference liquid and the external liquid are pumped into the test sink and the temporary sink respectively.

An installing box 100 has a reference sink 1, a test sink 2 and a temporary sink 3 (as shown in FIG. 1). The reference sink 1 has a reference liquid 6 which has a predetermined KH (alkalinity) value (as shown in FIG. 6). An interior diameter of the test sink 2 is equal to an interior diameter of the temporary sink 3.

A pH value detecting probe 5 is positioned in the test sink 2 and serves to test a liquid inputted into the test sink 2 for detecting a pH value of the liquid in the test sink 2.

Figure 3:
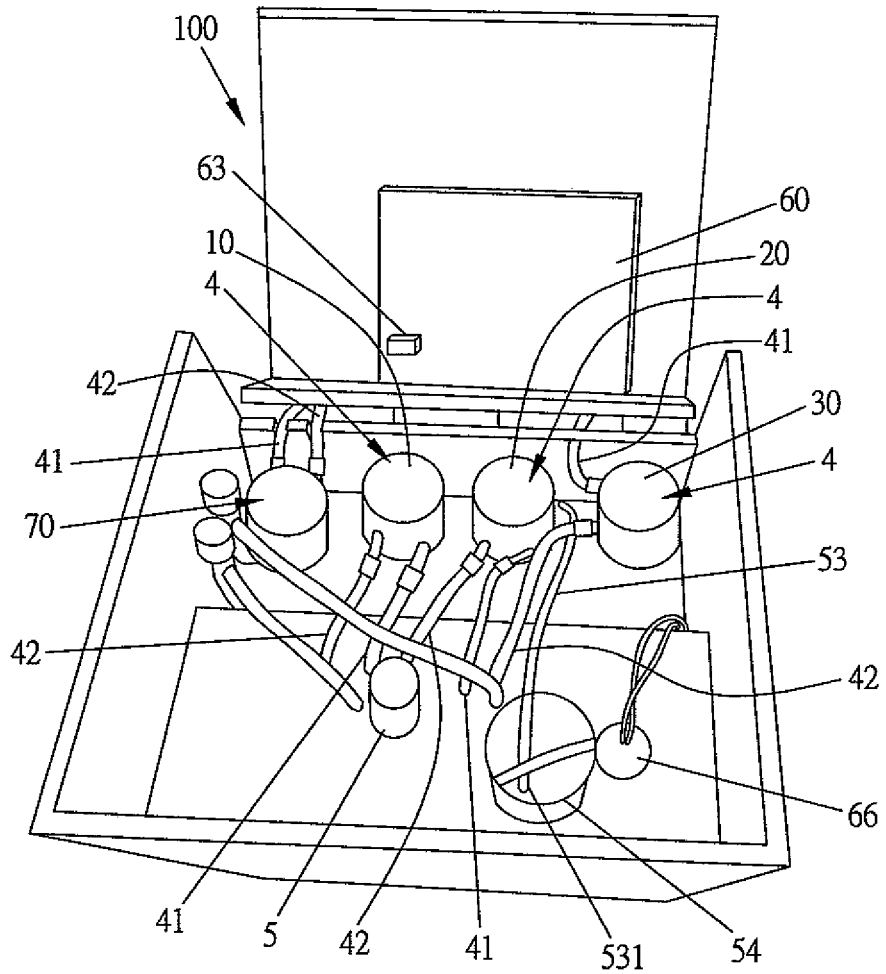
FIG. 3 is a schematic view showing the liquid pumping devices and the liquid titration device in the installing box.

Three liquid pumping devices 4 are a reference pumping device 10, a transferring pumping device 20 and a temporary pumping device 30, respectively (as shown in FIG. 3). Referring to FIG. 6, the reference pumping device 10 is connected to the reference sink 1 and the test sink 2. The transferring pumping device 20 is connected to the test sink 2 and the temporary sink 3. The temporary pumping device 30 is connected to the temporary sink 3 and serves to be connected to an external sink 200 which has an external liquid 7 to be tested.

In the present invention, the reference liquid 6 is a seawater. The external liquid 7 is a seawater used for culturing organisms.

The reference pumping device 10 serves to pump the reference liquid 6 of the reference sink 1 into the test sink 2.

The temporary pumping device 30 serves to pump the external liquid 7 of the external sink 200 into the temporary sink 3.

The transferring pumping device 20 serves to pump the external liquid 7 inputted to the temporary sink 3 into the test sink 2.

Figure 4:
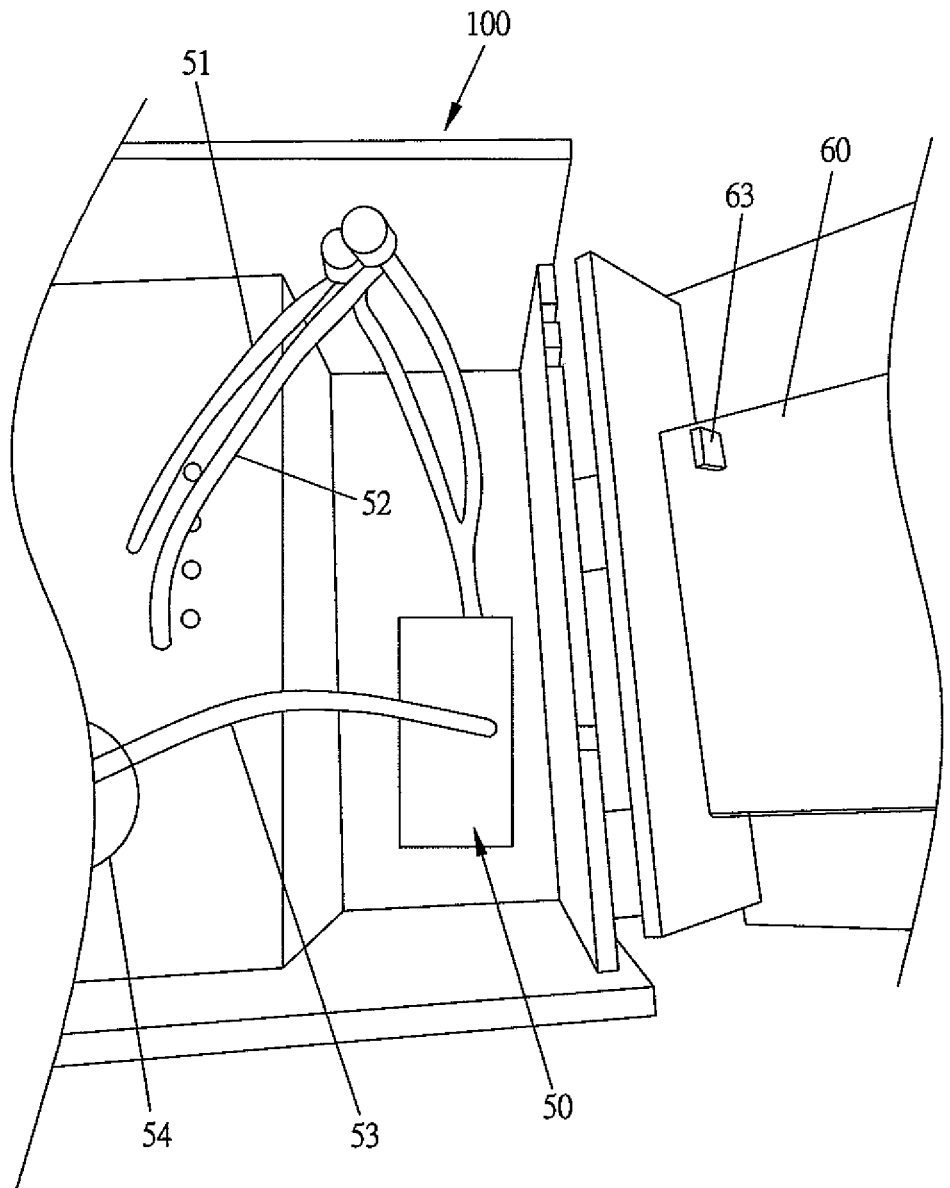
FIG. 4 is a schematic view showing the air pumping device in the installing box, wherein the liquid pumping devices and the liquid titration device are not shown.

An air pumping device 50 is connected to the test sink 2 and the temporary sink 3 (as shown in FIG. 4). The air pumping device 50 serves to pump air into the test sink 2 and the temporary sink 3 simultaneously.

A control device 60 is connected to the liquid pumping devices 4 and the pH value detecting probe 5. Referring to FIG. 6, in detecting, the control device 60 serves to control the air pumping device 50 to pump the air into the reference liquid 6 inputted to the test sink 2 and the external liquid 7 inputted to the temporary sink 3 simultaneously for a predetermined period of time to form a processed reference liquid 6' in the test sink 2 and a processed external liquid 7' in the temporary sink 3. Preferably, the predetermined period of time is 15 minutes.

Referring to FIG. 7, when the processed reference liquid 6' is formed in the test sink 2, the pH value detecting probe 5 is controlled by the control device 60 to detect a reference pH value of the processed reference liquid 6'.

When the testing of the processed reference liquid 6' is finished, the control device 60 serves to control the reference pumping device 10 to pump the processed reference liquid 6' tested by the pH value detecting probe 5 from the test sink 2 back into the reference sink 1 to empty the test sink 2, and to control the transferring pumping device 20 to pump the processed external liquid 7' from the temporary sink 3 into the test sink 2 emptied by the reference pumping device 10 (as shown in FIG. 8).

When the processed external liquid 7' is pumped into the test sink 2, the pH value detecting probe 5 is controlled by the control device 60 to detect an external pH value of the processed external liquid 7' inputted into the test sink 2.

Referring to FIG. 9, the control device 60 includes a processor 65. The processor 65 serves to receive the reference pH value and the external pH value detected by the pH value detecting probe 5 and to calculate an external KH value of the processed external liquid 7' according to the KH value of the reference liquid 6, the reference pH value and the external pH value.

A liquid titration device 70 is connected to the processor 65. The liquid titration device 70 serves to be connected to the external sink 200 and to receive an external input additive. The processor 65 serves to control the liquid titration device 70 to titrate a specific amount of the additive to the external sink 200 according to the external KH value for changing the KH value of the external liquid 7 of the external sink 200. Preferably, the additive is a baking soda solution.

The control device 60 is stored with a reference pumping time and a temporary pumping time. The control device 60 serves to control a pumping time of reference pumping device 10 and a pumping time of the temporary pumping device 30 by the reference pumping time and the temporary pumping time respectively to cause that a level of the reference liquid 6 inputted to the test sink 2 and a level of the external liquid 7 inputted to the temporary sink 3 are identical.

The control device 60 includes at least one control button 61 for changing the reference pumping time the temporary pumping time.

A reference liquid level detector 66 is installed in the reference sink 1 and is connected to the control device 60. The reference liquid level detector 66 serves to detect a level of the reference liquid 6 in the reference sink 1.

In the present invention, temperatures, atmospheric pressures on a liquid surface and dissolved $CO_2$ pressures of the processed reference liquid 6' and the processed external liquid 7' are identical or tend to be identical.

The external KH value of the processed external liquid 7' is $$KH_e = \frac{pH_e - pH_r}{M} + KH_r,$$

KHr is the external reference KH value, pHe is the external pH value, pHr is the reference pH value, and M is a specific coefficient.

It is known that a pH value of a liquid can be determined by: pH=f(KH, T, $P_0$, $P_C$), wherein KH is alkalinity, T is a temperature, $P_0$ is an atmospheric pressure on a liquid surface and $P_C$ is a dissolved $CO_2$ pressure of the liquid. The f(KH, T, $P_0$, $P_C$) can be approximated by Taylor polynomials.

In the present invention, the processed reference liquid 6' and the processed external liquid 7' are formed when temperatures, atmospheric pressures on a liquid surface and dissolved $CO_2$ pressures of the external liquid 7 and the reference liquid 6 are stabilized to be identical or to tend to be identical by pumping the air into the external liquid 7 in the temporary sink 3 and the reference liquid 6 in the test sink 2 with the air pumping device 50 for the predetermined period of time. Therefore, the external pH value ($pH_e$) and the reference pH value ($pH_r$) can be represented as:

$$pH_e=f(KH_e,T,P_0,P_C) \qquad (1)$$

$$pH_r=f(KH_r,T,P_0,P_C) \qquad (2)$$

The f($KH_e$, T, $P_0$, $P_C$) and k($KH_r$, T, $P_0$, $P_C$) can be approximated by Taylor polynomials respectively. By subtracting the Taylor polynomials of f($KH_r$, T, $P_0$, $P_C$) from the Taylor polynomials of f($KH_e$, T, $P_0$, $P_C$), the terms having T, $P_0$ and $P_C$ in the Taylor polynomials will be eliminated. Therefore by taking a first term of the Taylor polynomials of a result of subtracting above formula (2) from above formula (1), we can obtain:

$\Delta$pH=M×$\Delta$KH, wherein $\Delta$pH=$pH_e$–$pH_r$, $\Delta$KH=$KH_e$–$KH_r$, and M is a specific coefficient. FIG. 10 shows the relation of between the $KH_e$ and the $KH_r$.

As a result, the $KH_e$ can be represented by $$\frac{pH_e - pH_r}{M} + KH_r.$$

In the present invention, the test sink 2 and the temporary sink 3 are positioned within the reference sink 1. Each of the liquid pumping devices 4 has a first liquid tube 41 and a second liquid tube 42.

The first liquid tube 41 of the reference pumping device 10 is connected to the test sink 2 and the second liquid tube 42 of the reference pumping device 10 is connected to the reference sink 1.

The first liquid tube 41 of the transferring pumping device 20 is connected to the temporary sink 3 and the second liquid tube 42 of the transferring pumping device 20 is connected to the test sink 2.

The first liquid tube 41 of the temporary pumping device 30 serves to be connected to the external sink 200. The second liquid tube 42 of the temporary pumping device 30 is connected to the temporary sink 3.

The liquid titration device 70 has a first liquid tube 41 and a second liquid tube 42. The first liquid tube 41 of the liquid titration device 70 serves to receive the external input additive. The second liquid tube 42 of the liquid titration device 70 serves to be connected to the external sink 200.

Figure 5:
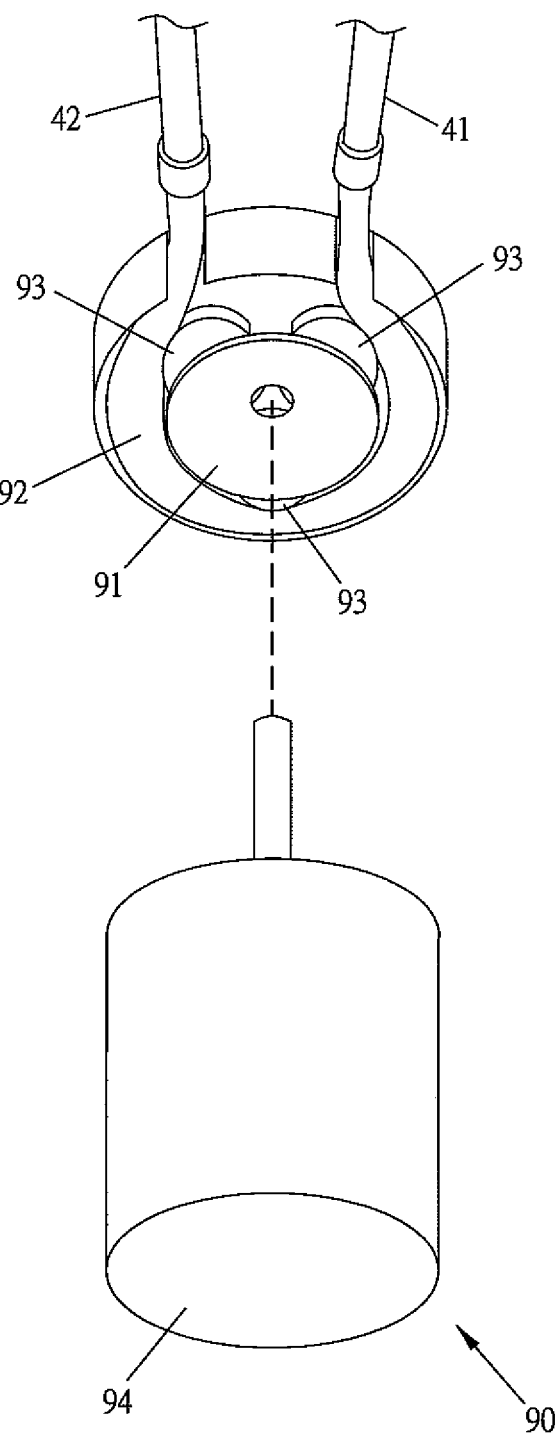
FIG. 5 is an exploded view of the peristaltic pump device.

Each of the liquid pumping devices 4 and the liquid titration device 70 includes a peristaltic pump device 90 respectively. Referring to FIG. 5, the peristaltic pump device 90 has a flexible tube 92 surrounding an outer side of a rotor 91. Two ends of the flexible tube 92 are connected to the corresponding first liquid tube 41 and the corresponding second liquid tube 42 respectively. A plurality of rollers 93 of the rotor 91 is driven by a motor 94 to be rotated clockwise or counterclockwise to compress the flexible tube 92 to cause that a liquid inputted from the first liquid tube 41 to the flexible tube 92 is moved to the second liquid tube 42, or to cause that a liquid inputted from the second liquid tube 42 to the flexible tube 92 is moved to the first liquid tube 41.

The air pumping device 50 is installed in the installing box 100 and includes a first air tube 51, a second air tube 52 and an input tube 53. An output end 511 of the first air tube 51 is positioned in the test sink 2. An output end 521 of the second air tube 52 is positioned in the temporary sink 3. The input tube 53 serves to receive external air for inputting the external air into the air pumping device 50. The air pumping device 50 further includes a sound suppressor 54 installed at an input end 531 of the input tube 53. The sound suppressor 54 serves to suppress a sound produced by the air inputted into the input tube 53.

Preferably, the two output ends 511, 521 of the first air tube 51 and the second air tube 52 are installed with two pumping stones 55 respectively for generating air bubbles.

The control device 60 serves to control the transferring pumping device 20 to pump the processed external liquid 7' tested by the pH value detecting probe 5 from the test sink 2 back to the temporary sink 3, and to control the temporary pumping device 30 to pump the processed external liquid 7' pumped back to the temporary sink 3 back to the external sink 200.

An electronic device 80 is connected to a transceiver 62 installed in the control device 60. The electronic device 80 includes a control unit 81. The transceiver 62 is connected to the processor 65 and serves to output the external KH value to the control unit 81 of the electronic device 80. The electronic device 80 is selected from mobile phone, tablet or a computer. The transceiver 62 is connected to the electronic device 80 through a wireless connection such as Wi-Fi.

The control unit 81 has a plurality of predetermined titration parameters which include a target KH value for the external liquid 7 of the external sink 200, a maximum amount of titration for the external liquid 7 of the external sink 200 in a specific period of time, and a required amount of titration for increasing a specific KH value of the external liquid 7 of the external sink 200.

The processor 65 serves to receive the titration parameters of the control unit 81. The processor 65 controls the liquid titration device 70 to output the additive by using the titration parameters of the control unit 81 when a value of subtracting the external KH value from the target KH value is larger than a specific threshold.

Figure 2:
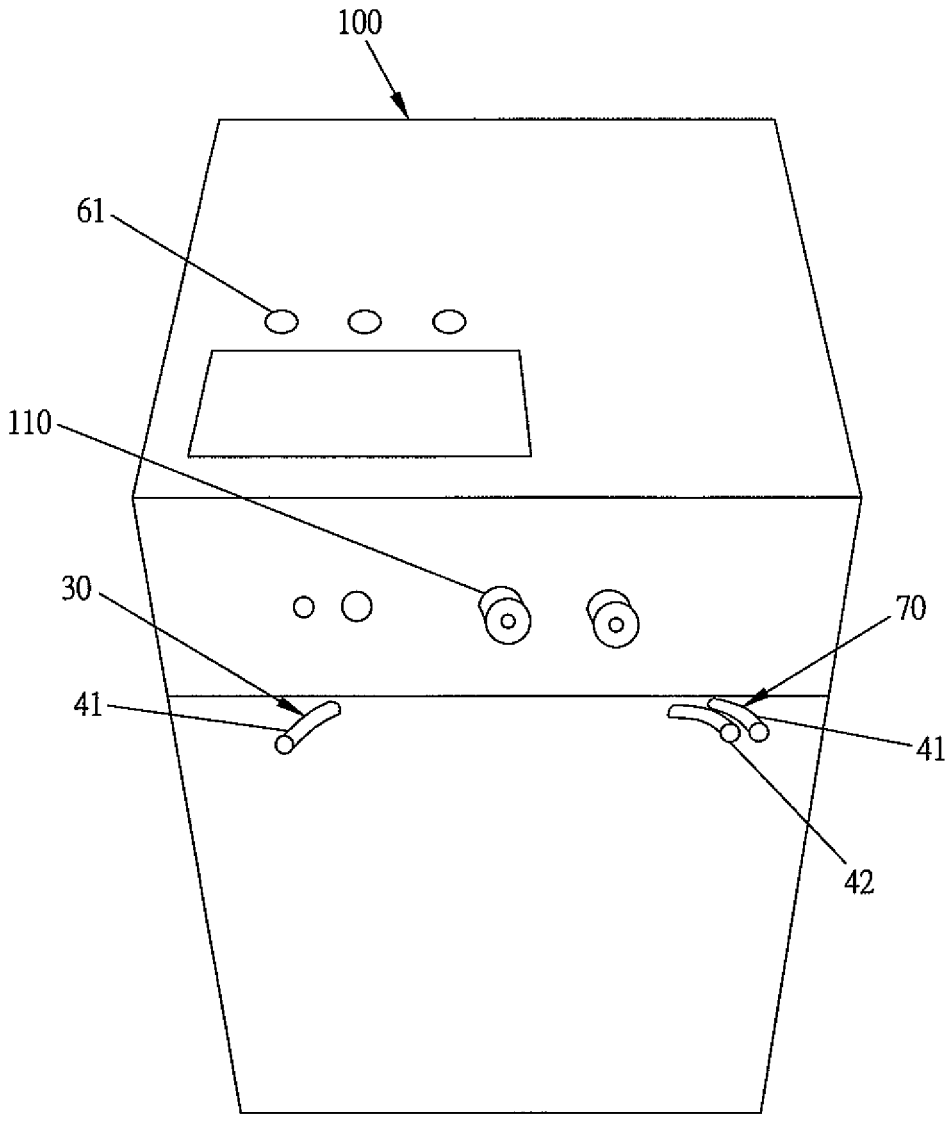
FIG. 2 is an assembly schematic view showing a back side of the installing box.

Referring to FIGS. 2 and 9, a KH to pH output port 110 is connected to the processor 65 and serves to convert the external KH value to a signal represented by a voltage form of pH value for outputting to other external devices.

The control device 60 also has an electric noise eliminator 63 which serves to eliminate a noise produced by testing of the pH value detecting probe 5.

In the present invention, both the reference pH value and the external pH value must be detected by the same pH value detecting probe 5 to avoid obtaining a wrong $\Delta$pH value ($pH_e$–$pH_r$). The reason is that every pH value detecting probe has its own unique non-linear drift error for detecting a pH value of a liquid. If the reference pH value and the external pH value are detected by using two different pH value detecting probes respectively, the correct $\Delta$pH value cannot be obtained due to different non-linear drift errors of the two pH value detecting probes.

In an initial state of the detection system of the present invention, the KH value of the reference liquid 6 of the reference sink 1 can be obtained (or calibrated) by withdrawing a small amount of the external liquid 7 from the external sink 200 and measuring the KH value of the withdrawn external liquid 7 by using a titration solution, and measuring the ΔpH value (pH$_e$–pH$_r$) by the pH value detecting probe 5. Therefore, the KH value of the reference liquid 6 can be obtained by the measured KH value of the withdrawn external liquid 7 and the ΔpH value. The KH value of the reference liquid 6 only needs to be calculated once at the initial state.

The advantages of the present invention are that the present invention has a control device capable of obtaining the KH value of the external liquid in an external sink at any time and adjusting the KH value of the external liquid in the external sink automatically by using a liquid titration device and titration parameters stored in an electronic device. The KH value of the external liquid is obtained by just pumping air into the reference liquid and the external liquid and detecting the pH values of the reference liquid and the external liquid, no titration portion or reagent is needed, which saves the cost of titration portion and reagent and avoids polluting the external sink by any chemicals of the titration portion and reagent. Therefore, the present invention can be used for auto detecting and adjusting the KH value of an external sink having a seawater used for culturing organisms. Moreover, the reference liquid and the external liquid tested will be pumped back to the reference sink and the external sink respectively, which do not cause any wasting of reference liquid or external liquid.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A water alkalinity detection system comprising:

an installing box (100) having a reference sink (1), a test sink (2) and a temporary sink (3); the reference sink (1) having a reference liquid (6) which has a predetermined KH (alkalinity) value;

a pH value detecting probe (5) positioned in the test sink (2) and serving to test a liquid inputted into the test sink (2) for detecting a pH value of the liquid in the test sink (2);

three liquid pumping devices (4) which are a reference pumping device (10), a transferring pumping device (20) and a temporary pumping device (30), respectively; the reference pumping device (10) being connected to the reference sink (1) and the test sink (2); the transferring pumping device (20) being connected to the test sink (2) and the temporary sink (3); the temporary pumping device (30) being connected to the temporary sink (3) and serving to be connected to an external sink (200) which has an external liquid (7) to be tested;

the reference pumping device (10) serving to pump the reference liquid (6) of the reference sink (1) into the test sink (2); the temporary pumping device (30) serving to pump the external liquid (7) of the external sink (200) into the temporary sink (3); the transferring pumping device (20) serving to pump the external liquid (7) inputted to the temporary sink (3) into the test sink (2);

an air pumping device (50) connected to the test sink (2) and the temporary sink (3); the air pumping device (50)

serving to pump air into the test sink (2) and the temporary sink (3) simultaneously;

a control device (60) connected to the liquid pumping devices (4) and the pH value detecting probe (5); wherein in detecting, the control device (60) serves to control the air pumping device (50) to pump the air into the reference liquid (6) inputted to the test sink (2) and the external liquid (7) inputted to the temporary sink (3) simultaneously for a predetermined period of time to form a processed reference liquid (6') in the test sink (2) and a processed external liquid (7') in the temporary sink (3); the pH value detecting probe (5) is controlled by the control device (60) to detect a reference pH value of the processed reference liquid (6'); the control device (60) serves to control the reference pumping device (10) to pump the processed reference liquid (6') tested by the pH value detecting probe (5) from the test sink (2) back into the reference sink (1) to empty the test sink (2), and to control the transferring pumping device (20) to pump the processed external liquid (7') from the temporary sink (3) into the test sink (2) emptied by the reference pumping device (10); the pH value detecting probe (5) is controlled by the control device (60) to detect an external pH value of the processed external liquid (7') inputted into the test sink (2); and the control device (60) including a processor (65); the processor (65) serving to receive the reference pH value and the external pH value detected by the pH value detecting probe (5) and to calculate an external KH value of the processed external liquid (7') according to the KH value of the reference liquid (6), the reference pH value and the external pH value.

2. The water alkalinity detection system as claimed in claim 1, further comprising a liquid titration device (70) connected to the processor (65); the liquid titration device (70) serving to be connected to the external sink (200) and to receive an external input additive; and the processor (65) serving to control the liquid titration device (70) to titrate a specific amount of the additive to the external sink (200) according to the external KH value for changing the KH value of the external liquid (7) of the external sink (200).

3. The water alkalinity detection system as claimed in claim 2, further comprising:

an electronic device (80) connected to a transceiver (62) installed in the control device (60); the electronic device (80) including a control unit (81); the transceiver (62) being connected to the processor (65) and serving to output the external KH value to the control unit (81) of the electronic device (80);

wherein the control unit (81) has a plurality of predetermined titration parameters which include a target KH value for the external liquid (7) of the external sink (200), a maximum amount of titration for the external liquid (7) of the external sink (200) in a specific period of time, and a required amount of titration for increasing a specific KH value of the external liquid (7) of the external sink (200); and wherein the processor (65) serves to receive the titration parameters of the control unit (81); the processor (65) controls the liquid titration device (70) to output the additive by using the titration parameters of the control unit (81) when a value of subtracting the external KH value from the target KH value is larger than a specific threshold.

4. The water alkalinity detection system as claimed in claim 2, wherein the test sink (2) and the temporary sink (3)

are positioned within the reference sink (1); each of the liquid pumping devices (4) has a first liquid tube (41) and a second liquid tube (42); the first liquid tube (41) of the reference pumping device (10) is connected to the test sink (2) and the second liquid tube (42) of the reference pumping device (10) is connected to the reference sink (1); the first liquid tube (41) of the transferring pumping device (20) is connected to the temporary sink (3) and the second liquid tube (42) of the transferring pumping device (20) is connected to the test sink (2); the first liquid tube (41) of the temporary pumping device (30) serves to be connected to the external sink (200); the second liquid tube (42) of the temporary pumping device (30) is connected to the temporary sink (3); and wherein the liquid titration device (70) has a first liquid tube (41) and a second liquid tube (42); the first liquid tube (41) of the liquid titration device (70) serves to receive the external input additive; and the second liquid tube (42) of the liquid titration device (70) serves to be connected to the external sink (200).

5. The water alkalinity detection system as claimed in claim 4, wherein each of the liquid pumping devices (4) and the liquid titration device (70) includes a peristaltic pump device (90) respectively;

the peristaltic pump device (90) has a flexible tube (92) surrounding an outer side of a rotor (91); two ends of the flexible tube (92) are connected to the corresponding first liquid tube (41) and the corresponding second liquid tube (42) respectively; a plurality of rollers (93) of the rotor (91) is driven by a motor (94) to be rotated clockwise or counterclockwise to compress the flexible tube (92) to cause that a liquid inputted from the first liquid tube (41) to the flexible tube (92) is moved to the second liquid tube (42), or to cause that a liquid inputted from the second liquid tube (42) to the flexible tube (92) is moved to the first liquid tube (41).

6. The water alkalinity detection system as claimed in claim 1, wherein temperatures, atmospheric pressures on a liquid surface and dissolved $CO_2$ pressures of the processed reference liquid (6') and the processed external liquid (7') are identical or tend to be identical.

7. The water alkalinity detection system as claimed in claim 1, wherein the predetermined period of time is 15 minutes.

8. The water alkalinity detection system as claimed in claim 1, wherein the control device (60) serves to control the transferring pumping device (20) to pump the processed external liquid (7') tested by the pH value detecting probe (5) from the test sink (2) back to the temporary sink (3), and to control the temporary pumping device (30) to pump the processed external liquid (7') pumped back to the temporary sink (3) back to the external sink (200).

9. The water alkalinity detection system as claimed in claim 1, wherein the control device (60) is stored with a reference pumping time and a temporary pumping time; the control device (60) serves to control a pumping time of reference pumping device (10) and a pumping time of the temporary pumping device (30) by the reference pumping time and the temporary pumping time respectively to cause that a level of the reference liquid (6) inputted to the test sink (2) and a level of the external liquid (7) inputted to the temporary sink (3) are identical.

10. The water alkalinity detection system as claimed in claim 1, wherein the air pumping device (50) is installed in the installing box (100) and includes a first air tube (51), a second air tube (52) and an input tube (53); an output end (511) of the first air tube (51) is positioned in the test sink (2); an output end (521) of the second air tube (52) is positioned in the temporary sink (3); the input tube (53) serves to receive external air for inputting the external air into the air pumping device (50); and the two output ends (511), (521) of the first air tube (51) and the second air tube (52) are installed with two pumping stones (55) respectively for generating air bubbles.

11. The water alkalinity detection system as claimed in claim 10, wherein the air pumping device (50) further includes a sound suppressor (54) installed at an input end (531) of the input tube (53); and the sound suppressor (54) serves to suppress a sound produced by the air inputted into the input tube (53).

12. The water alkalinity detection system as claimed in claim 1, further comprising a KH to pH output port (110) connected to the processor (65) and serving to convert the external KH value to a signal represented by a voltage form of pH value for outputting to other external devices.

13. The water alkalinity detection system as claimed in claim 1, further comprising a reference liquid level detector (66) installed in the reference sink (1) and connected to the control device (60);

the reference liquid level detector (66) serving to detect a level of the reference liquid (6) in the reference sink (1).

14. The water alkalinity detection system as claimed in claim 1, wherein the reference liquid (6) is a seawater; and the external liquid (7) is a seawater used for culturing organisms.

15. The water alkalinity detection system as claimed in claim 1, wherein the control device (60) has an electric noise eliminator (63) serving to eliminate a noise produced by testing of the pH value detecting probe (5).

* * * * *